United States Patent
Zhang et al.

(10) Patent No.: US 9,926,251 B2
(45) Date of Patent: Mar. 27, 2018

(54) METHOD FOR SEPARATION OF CLOSE-BOILING MIXTURE OF POLYOLS

(71) Applicant: DALIAN INSTITUTE OF CHEMICAL PHYSICS, CHINESE ACADEMY OF SCIENCES, Dalian, Liaoning (CN)

(72) Inventors: Tao Zhang, Liaoning (CN); Shuo Al, Liaoning (CN); Mingyuan Zheng, Liaoning (CN); Aiqin Wang, Liaoning (CN); Weizhen Li, Liaoning (CN); Xiaodong Wang, Liaoning (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 0 days.

(21) Appl. No.: 15/521,033

(22) PCT Filed: Nov. 26, 2015

(86) PCT No.: PCT/CN2015/095593
§ 371 (c)(1),
(2) Date: Apr. 21, 2017

(87) PCT Pub. No.: WO2016/082766
PCT Pub. Date: Jun. 2, 2016

(65) Prior Publication Data
US 2017/0327446 A1    Nov. 16, 2017

(30) Foreign Application Priority Data
Nov. 28, 2014    (CN) .......................... 2014 1 0714170

(51) Int. Cl.
*C07C 29/80* (2006.01)
*C07C 31/18* (2006.01)
*C07C 1/24* (2006.01)
*B01D 3/06* (2006.01)
*B01D 3/10* (2006.01)
*B01D 15/08* (2006.01)
*B01J 29/40* (2006.01)

(52) U.S. Cl.
CPC .............. *C07C 29/80* (2013.01); *B01D 3/065* (2013.01); *B01D 3/10* (2013.01); *B01D 15/08* (2013.01); *C07C 1/24* (2013.01); *C07C 31/18* (2013.01); *B01J 29/40* (2013.01)

(58) Field of Classification Search
CPC ............ C07C 29/80; C07C 31/18; C07C 1/24
USPC ....................................... 568/868
See application file for complete search history.

(56) References Cited

FOREIGN PATENT DOCUMENTS

| CN | 102643164 A | 8/2012 |
| CN | 102911013 A | 2/2013 |
| CN | 104098439 A | 10/2014 |

*Primary Examiner* — Sikarl Witherspoon
(74) *Attorney, Agent, or Firm* — Novick, Kim & Lee, PLLC; Allen Xue

(57) ABSTRACT

This invention discloses an approach for the separation of the close-boiling mixture of polyols. The raw material is ethylene glycol containing miscellaneous polyols (such as 1,2-propylene glycol and 1,2-butanediol). Over an acid catalyst, these miscellaneous polyols, through (1) a dehydration reaction, (2) pinacol rearrangement, and (3) acetalization or ketalization reaction, are converted into aldehydes (small amounts), acetals, and ketals (trace amount), which are simultaneously and readily separated via distillation. Meanwhile, after the reaction, the mixture is further separated to obtain an ethylene glycol product at a high purity. The invention provides a technique to remove the miscellaneous polyols from ethylene glycol via liquid-phase dehydration reactions under mild conditions, with low energy consumption. In particular, this approach is markedly effective for the removal of 1,2-butanediol that is difficult to be removed via conventional techniques. The purity of the resulting ethylene glycol product is high, and value-added acetals or ketals are co-produced.

11 Claims, 1 Drawing Sheet

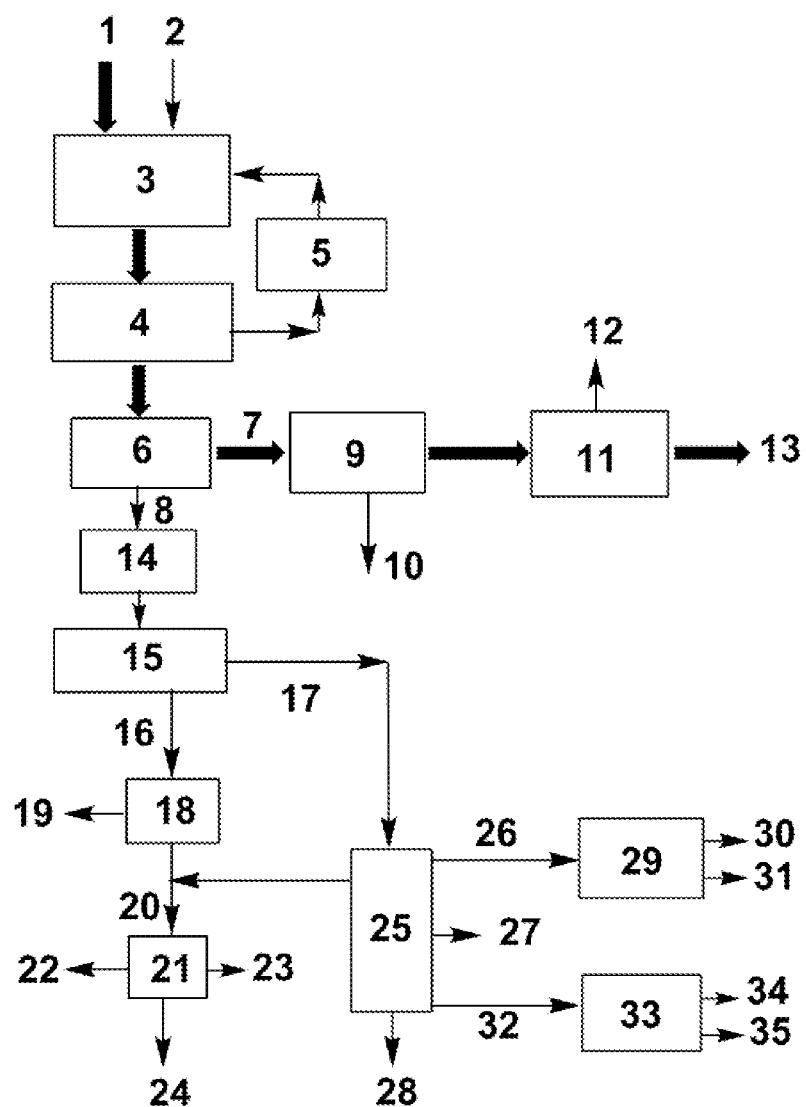

METHOD FOR SEPARATION OF CLOSE-BOILING MIXTURE OF POLYOLS

FIELD OF INVENTION

The present invention discloses a method for the separation of the close-boiling mixture of polyols, belonging to the technical field of chemical separation.

BACKGROUND TO THE INVENTION

Ethylene glycol, also known as glycol or ethanediol, is a commodity chemical and can be used to produce polyester, polyethylene terephthalate, explosives, solvents, antifreezes, plasticizers, and hygroscopic agents. Due to the confinement of technical monopoly and limited oil production, the supply of ethylene glycol in China has depended on the import for a long time. Since 2002, the import of ethylene glycol of China has accounted for >70% of the quantity demanded wherein the consumption of ethylene glycol in polyester industry contributes >80%.

The conventional syntheses of ethylene glycol are based on the petrochemical industry, which mainly use ethane as the raw material to produce ethylene glycol through the addition reaction between the intermediate of ethylene oxide and water. Simultaneously, by-products of diethylene glycol, triethylene glycol, and other low-value chemicals are formed. The key techniques are mainly possessed by Shell (the United Kingdom/Netherlands), Halcon-SD (the United States), Dow Chemical (the United States), and UCC (the United States). In addition, the processes of hydration and separation consume a large amount of water, energy, petroleum and natural gas. A pathway through the intermediate of ethylene carbonate is a novel synthesis method of ethylene glycol, which takes advantage of the highly pure carbon dioxide discharged by the unit of production of ethylene oxide. This method can reduce the emission of carbon, and barely consumes water, which also reduces the consumption of energy in separation. A more marked merit of this method is the co-production of dimethyl carbonate. However, this synthesis pathway also consumes ethylene oxide, still depends on petroleum, and the key techniques are also kept by several companies.

With the progress of science and technology, coal- or biomass-based syntheses of ethylene glycol have shown many advantages gradually, such as reducing the dependence on petroleum and breakup of the technical monopoly. Preferably, the biomass-based synthesis pathway primarily utilizes low-cost, fast-growing, and carbon-neutral cellulose-enriched xylophyta or herbs as its feedstock. Hence, both the costs and greenhouse effect of the production of ethylene glycol are effectively reduced. Thus, this biomass-based synthesis pathway is a promising technology.

Coal-based ethylene glycol can be synthesized via the electrochemical hydrogenation and dimerization of formaldehyde, polymerization of methanol, or hydrogenation of oxalate. The yield of ethylene glycol through the electrochemical hydrogenation and dimerization of formaldehyde is high, while the electricity consumption is high and purity of raw ethylene glycol is low, resulting in high costs of purification. The method via the hydrogenation of oxalate is the most promising synthesis pathway of coal-based ethylene glycol, which utilizes CO in the syngas as the intermediate to produce oxalate through oxidation-coupling reactions and then synthesize ethylene glycol through the catalytic hydrogenation of oxalate. On account of excessive hydrogenation, part of the system is converted into methanol and ethanol, which will be reacted with ethylene glycol to form 1,2-propanediol and 1,2-butanediol respectively via the Guerbet reaction. Wherein, the boiling points of 1,2-butanediol and ethylene glycol are the closest, and both diols can also form an azeotrope. Therefore, the energy consumption of distillation in the industry is high, which is an important reason for the difficult industrialization of coal-based synthesis of ethylene glycol.

Because of the limited selectivity of catalysts for the biomass-based synthesis of ethylene glycol, during the hydrogenation process, apart from the main product of ethylene glycol, miscellaneous diols and triols at a total yield of ~30 wt % to 40 wt % are generated, such as 1,2-propanediol, 1,2-butanediol, 1,3-butanediol, 2,3-butanediol, glycerin, and so on, wherein these miscellaneous diols have a boiling point higher or lower than that of ethylene glycol by ~10° C. and certain diols can form an azeotrope with ethylene glycol, resulting in the significant decrease of separation efficiency by distillation and increase of energy consumption. The physical and chemical properties of these miscellaneous diols are similar to those of ethylene glycol, and hence it is difficult to separate them via conventional techniques including distillation, extraction, adsorption, etc. In addition, the viscosity of the mixture of these polyols is high at room or low temperatures. Especially within narrow space, the flow resistance will be great, increasing the energy consumption of transportation. Meanwhile, the expected output of ethylene glycol, as a commodity chemical, is high while the processing capacity of liquid-phase adsorption is low. Therefore, adsorptive separation is also not applicable to the separation of these polyols.

SUMMARY OF THE INVENTION

The inventors have discovered a new and efficient method for the separation of polyols and purification of ethylene glycol. This method provides a simple process that converts the refractory miscellaneous polyols into easily separable value-added acetals or ketals. The energy consumption, cost, and low discharge amount of wastes of the process is low. This process is an economic, highly efficient, energy-saving, and environmentally sound separation pathway. Specifically, the raw ethylene glycol contains one or several polyols as the follows: 1,2-propanediol, 1,3-propanediol, 1,2-butanediol, 1,2-pentanediol, 1,2-hexanediol, 1,3-butanediol, 2,3-butanediol, 1,4-butanediol, and glycerol. Typically, the raw ethylene glycol is synthesized via the coal-based or biomass-based pathways. The mass fraction of ethylene glycol in the raw ethylene glycol is in the range of 50%-95% and mass fraction of miscellaneous polyols ranges from 5% to 50%.

Typically, the raw ethylene glycol is mixed with an acid catalyst at 150-198° C. and atmospheric pressure in a dehydration reactor. The miscellaneous polyols are converted into volatile products via dehydration, acetalization, and ketalization reactions. The volatile products are further removed via vaporization or distillation, and hence the miscellaneous polyols are removed. The acid catalyst includes liquid Brønsted acids, solid Brønsted acids, Lewis acids, acid-site-containing oxides, an acid-site-containing mineral, other Brønsted acids, or their combinations, wherein the most active catalysts include H-form molecular sieves, sulfonated activated carbon, H-form resins, sulfuric acid, hydrochloric acid, and nitric acid. The catalyst accounts for 0.1 wt %-15 wt % of the system of the dehydration reaction. After the reaction, the product of ethylene glycol is further purified to remove the residual miscellaneous polyols via distillation, extraction, crystallization, adsorption, chromatography, or their combinations.

The unconverted material in the dehydration reactor contains ethylene glycol and acid catalysts. When only solid acid catalysts are used, the catalysts are removed from ethylene glycol through solid-liquid separation, evaporation or distillation. The device for solid-liquid separation can be a pressure filter, vacuum filter, settler, or centrifuge. The removed solid acid is regenerated via calcination or elution or drying for the recycling of solid catalysts. When only liquid acid catalysts are used, the catalysts are removed from ethylene glycol through evaporation or distillation for the recycling of liquid catalysts. Otherwise, the liquid acid catalysts are neutralized with an alkali and then the product of the neutralization reaction is removed from ethylene glycol through evaporation or crystallization.

When both solid and liquid acid catalysts are used, the solid catalysts are firstly removed from ethylene glycol through solid-liquid separation, and then the liquid acid catalysts are removed from ethylene glycol through evaporation or distillation; the ethylene glycol can also be directly separated from both solid and liquid acid catalysts via evaporation or distillation.

The removed volatile products of miscellaneous polyols via dehydration, acetalization, and ketalization reactions are vaporized, condensed, and collected. The removed products include volatile oil-phase and aqueous products. The oil-phase and aqueous products are then separated. The oil-phase product can be further separated into acetals, ketals, dioxanes, aldehydes, and ketones. Apart from the removal of miscellaneous polyols, by-products of acetals, ketals, cyclic ethers, acyclic ethers, aldehydes, and ketones are co-produced. The dehydration reactor itself also functions as a simple reactive distillation apparatus to remove the by-products from ethylene glycol. Otherwise, these by-products can also be produced and removed via multi-stage reactive distillation. Otherwise, the reaction system can also be refluxed in the reactor, and then the mixture is separated through decantation, extraction, adsorption, or distillation.

DETAILED DESCRIPTION OF THE INVENTION

The specific procedures to implement the above-mentioned method are described as follows:

(a) Dehydration reaction: The mass fraction of ethylene glycol in the feedstock is in the range of 50%-95%, and the others are miscellaneous polyols, such as 1,2-propanediol, 1,3-propanediol, 1,2-butanediol, 1,3-butanediol, 2,3-butanediol, 1,4-butanediol, and glycerin, with a total content of 5 wt % to 50 wt %. In a dehydration reactor, the crude ethylene glycol is heated to 150-198° C. Then, 0.1 wt % to 15 wt % of an acid catalyst was added in the reaction system with stirring. The miscellaneous polyols are converted via dehydration reactions into a low-boiling-point oil-phase product and an aqueous solution, which are readily to be removed. The conversion of 1,2-butanediol is in the range of 55% to 99.8% and conversion of 1,2-propanedio is in the range of 50% to 99.6%.

(b) Removal of volatile products: At the high temperature in the dehydration reactor, the low-boiling-point products in the previous step are evaporated, condensed, and collected, and the oil-phase product is separated from the aqueous solution via decantation. The oil-phase product contains 2-methyl-1,3-dioxolane, 2-ethyl-1,3-dioxolane, 2-ethyl-4-methyl-1,3-dioxolane, 2-propyl-1,3-dioxolane, 4-methyl-2-propyl-1,3-dioxolane, 2-isopropyl-4-methyl-1,3-dioxolane, 2-ethyl-2-methyl-1,3-dioxolane, 1,4-dioxane and so on. Moreover, a small amount of acetone, propanal, butanal, and butanone is produced. The dehydration reactor itself also functions as a simple reactive distillation apparatus, to remove the reaction products from the ethylene glycol. Also, the reaction products can be removed via multi-stage reactive distillation. Alternatively, the reaction system can be refluxed in the reactor, and then the products are separated from ethylene glycol via decantation, extraction, adsorption or distillation.

(c) Separation of catalysts: the liquid that was not removed via the vaporization in the reactor contains an acid catalyst and intermediate product of ethylene glycol. If a solid acid catalyst was utilized, the catalyst is separated from the intermediate product via solid-liquid separation, evaporation, or distillation. If a liquid acid was utilized, the catalyst is separated from ethylene glycol through evaporation or distillation for the recycling. Otherwise, the liquid acid is neutralized with an alkali and then removed via crystallization or distillation.

(d) Vacuum distillation: during the dehydration reaction in the first step, a small amount of high-boiling-point diethylene glycol, triethylene glycol, tetraethylene glycol, and crown ethers was co-produced. These impurities are removed via vacuum distillation to purify the intermediate product of ethylene glycol. The oligomerization of ethylene glycol can be inhibited and the yield of ethylene glycol can be improved at a low temperature of 116 to 135° C. and an absolute pressure of 3-17 kPa in the bottom.

(e) Complete removal of miscellaneous polyols: the primary impurities in the overhead of the vacuum distillation in the fourth step are miscellaneous diols such as 1,2-propanediol, which are removed via distillation, extraction, crystallization, adsorption, or chromatography, and an ethylene glycol product at a high purity is thus obtained.

(f) Concentration of aldehydes and ketones in the aqueous product: the main component of the aqueous product in the second step is water. The solutes are a certain amount of acetone, propanal, acetaldehyde, etc. The boiling points of these solutes are lower than the azeotropic temperature of water/1,4-dioxane by ~30° C., and hence these three aldehydes and ketones are separated and concentrated via stripping or distillation. Then, the mixture of aldehydes and ketones is further separated through distillation.

(g) Preliminary separation of the oil-phase product: the oil-phase product in the second step also contains a small amount of acetone, propanal, and acetaldehyde. Through distillation, the oil-phase product is separated into five products: aldehydes/ketones, low-boiling-point acetals, crude dioxane, high-boiling-point acetals, and high-boiling-point oxygenates. The separated aldehydes and ketones are combined with the concentrated aldehydes/ketones in the previous step. The mixture is further separated through distillation to produce acetone, propanal, and acetaldehyde.

(h) Purification of acetals and ketals: the low-boiling-point acetals contains 2-ethyl-1,3-dioxolane, 2-ethyl-4-methyl-1,3-dioxolane, and so on. The high-boiling-point acetals contains 2-propyl-1,3-dioxolane, 2-isopropyl-4-methyl-1,3-dioxolane, etc. The boiling points of these acetals (or a small amount of ketals) range from 100 to 138° C. at atmospheric pressure. Hence, the low-boiling-point and high-boiling-point acetals are independently separated via distillation, chromatography, or gradient elution. Thus, several pure products of these acetals (or ketals) are obtained.

(i) Regeneration of catalysts: the solid acid catalysts in the third step are regenerated through calcination, elution, or drying for the recycling.

Preferably, the dehydration reaction in the first step is in manner of reactive simple distillation or reactive multi-stage distillation.

Preferably, the dehydration reaction in the first step is carried out at 180-186° C.

A preferred catalyst for the dehydration reaction is a Hβ ($SiO_2/Al_2O_3$ ratio=25 or 160) or HZSM-5 ($SiO_2/Al_2O_3$ ratio=25) molecular sieve. The mass fraction of the catalyst accounts for 4 wt % of the reaction system.

Preferably, the dehydration reaction is performed at atmospheric pressure in a liquid-phase system.

Preferably, after the reaction, the solid-liquid separation of the system containing solid catalysts is instantly conducted at the high temperature of the system.

The required equipments or devices for the present invention are the following: catalytic dehydration reactor, fixed-bed reactor or reactive distillation column; solid-liquid separation equipment; vacuum distillation equipment; condenser; oil splitter; atmospheric distillation equipment or chromatography apparatus.

The mechanism of the present invention for the separation of polyols and production of by-products of acetals (or a small amount of ketals) are the following:

Firstly, a catalytic dehydration reaction takes place: over an acid catalyst, a hydroxyl group of a molecule of vicinal diol (ethylene glycol, 1,2-propanediol, 1,2-butanediol, 2,3-butanediol, etc.) is protonated, resulting in the elimination of a molecule of water to form a carbenium ion.

The selectivity of the dehydration reaction in the first step depends on the stability of the carbenium ion: the carbenium ion formed by vicinal butanediol (secondary carbon) has the highest stability, and the one formed by vicinal propanediol (secondary carbon) has the second highest stability. In contrast, ethylene glycol (primary carbon) can hardly form a stable carbenium ion. Therefore, the conversion of 1,2-butanediol in the dehydration reaction is the highest, and 1,2-butanediol is the most refractory impurity in conventional distillation. It is noted that a small number of primary carbon atoms in 1,2-propanediol and 1,2-butanediol also form carbenium ions.

Pinacol rearrangement: the positive center of the carbenium ion is transferred to the carbon atom neighboring another hydroxyl group (i.e., rearrangement) to form a relatively stable oxonium ion. The reason is that the lone pairs of the oxygen atoms conjugate with the positive center, and a more stable conjugated structure is thus formed. Simultaneously, the transfer of alkyls or hydrogen occurs. Noticeably, the carbenium ions formed by the primary carbon atoms in 1,2-propanediol and 1,2-butanediol, in the previous step, are also rearranged to form oxonium ions.

Then, both types of oxonium ions lose a proton to form stable aldehydes or ketones respectively, wherein the yield of aldehydes is much higher.

Secondary dehydration reactions: the aldehydes and ketones are reacted with ethylene glycol and propylene glycol at high temperatures over an acid catalyst via acetalization or ketalization reactions, resulting in the formation of four acetals: 2-ethyl-1,3-dioxolane, 2-ethyl-4-methyl-1,3-dioxolane, 2-propyl-1,3-dioxolane, and 2-isopropyl-4-methyl-1,3-dioxolane, wherein the 2-isopropyl-4-methyl-1,3-dioxolane was formed by isobutylaldehyde and isobutylaldehyde is the product of isomerization of n-butanal over an acid catalyst. Because of the steric hindrance effect of the alkyl groups beside the carbonyl group of ketones, the ketalization reactions are difficult to take place, and hence most of the acetone is evaporated directly. Consequently, the content of ketals in the products is very low (even trace amount). Generally, it is not necessary to remove the ketals in the products of acetal. On the other hand, the primary component of the product of aldehydes and ketones is acetone, followed by propanal and acetaldehyde, under most circumstances. All the butanal and butanone (trace amount) are reacted via acetalization or ketalization reactions.

Compared with the conventional techniques, the advantages of the present invention are the following:

(a) The present invention is highly selective to 1,2-butanediol and 1,2-propanediol. The removal of 1,2-butanediol is as high as 55%-99.8% and removal of 1,2-propylene glycol is up to 50%-99.6%. The purified ethylene glycol product can meet the requirements of downstream polyester industry.

(b) The main reaction of dehydration can take place completely in a liquid-phase system at atmospheric pressure, which only requires a small amount of low-temperature heat and a reactor at atmospheric pressure. Under the condition of equivalent output of 99 wt % ethylene glycol, total energy consumption of the present invention is 50%-75% of that of conventional distillation. The process is low-cost, energy-saving, and environmentally sound.

(c) The high-boiling-point products in the bottom of vacuum distillation column for the refining of ethylene glycol are mainly low-freezing-point acyclic ethers, the mixture of which can be utilized as an antifreeze for vehicles.

(d) The quality of ethylene glycol is improved (UV absorbance is low). In the coal-based synthesis pathway (through dimethyl oxalate intermediate) and biomass-based synthesis pathway of ethylene glycol, certain side effects lead to the formation of carbonyl-containing impurities such as aldehydes, ketones, and diketones. Although the concentrations of these impurities are low, they can strongly absorb UV light, which has a significant negative impact on the quality of ethylene glycol. In the present process, these carbonyl-containing impurities are converted into acetals or ketals that has no capability of UV absorption, and thus the quality of ethylene glycol is improved. In addition, the aldehydes or ketones formed in the present invention have low boiling points and can be completely separated during the process. It is confirmed by gas chromatography that the purified ethylene glycol product did not contain these aldehydes or ketones formed in the dehydration reactions.

(e) Three products of aldehydes or ketones are obtained. The boiling point of acetaldehyde is lower than that of acetone and propanal by ~27° C., and hence acetaldehyde can be easily separated from acetone and propanal via distillation. The boiling-point difference between acetone and propanal is ~8.5° C., and they will not form an azeotrope. Moreover, the boiling points of them are <60° C. Therefore, the separation of acetone and propanal can be realized via distillation at a low cost of low-temperature heat.

(f) A by-product of raw dioxane is obtained. The raw dioxane contains 1,4-dioxane and other low-boiling-point ethers, which can be utilized to produce solvents, lacquers, varnishes, plasticizers, and wetting agents.

(g) A by-product of high-boiling-point oxygenatesis obtained. The flash points of such substances are generally higher than 50° C., and thus they can be used as additives to fuels, which can reduce the content of particulates in the exhaust gases of vehicles.

(h) The acetals and ketals (trace amount) are substances with fragrance of fruits or flowers and can be utilized as an intermediate for the synthesis of value-added flavors, fragrances and other chemicals. For the same weight of products, the economic value of acetals (or ketals) is far higher than that of ethylene glycol. Although the yield of acetals and ketals is not high, the output of acetals and ketals is considerable because the output of ethylene glycol is high in the industry. The by-products of acetals and ketals (trace amount) can increase the economic value of the entire process of the present invention.

For the afore-mentioned reasons, the present invention can efficiently remove the miscellaneous polyols in ethylene glycol and can co-produce value-added by-products, reducing pollution and consumption of energy. And, the present invention has significant economic advantages.

BRIEF DESCRIPTION OF THE DRAWING

Schematic flow diagram of the process in the present invention is illustrated in the FIGURE, and the numbers in the FIGURE denote the materials or equipment as follows: 1. feedstock of polyols 2. catalyst 3. dehydration reactor 4. catalyst separator 5. catalyst regenerator 6. vapor-liquid separator 7. liquid phase 8. gas phase 9. vacuum distillation equipment 10. high-boiling-point diethylene glycol, triethylene glycol, glycerol, etc 11. vacuum distillation equipment 12. miscellaneous polyols (such as 1,2-propanediol) 13. main product (ethylene glycol) 14. condenser 15. decantor 16. aqueous product 17. oil-phase raw product 18. distillation equipment 19. water 20. aldehydes and ketones 21. distillation equipment 22. acetaldehyde 23. propanal 24. acetone 25. distillation equipment 26. low-boiling-point acetals 27. raw dioxane 28. high-boiling-point oxygenates 29. distillation or chromatography equipment 30. 2-ethyl-1,3-dioxolane 31. 2-ethyl-4-methyl-1,3-dioxolane 32. high-boiling-pointacetals 33. distillation or chromatography equipment 34. 2-isopropyl-4-methyl-1,3-dioxolane 35. 2-propyl-1,3-dioxolane.

Embodiments

The present invention is described in detail with the FIGURE and the following examples:

EXAMPLE 1

(a) Dehydration reaction: 100 mL of crude ethylene glycol (73 wt % ethylene glycol, 17 wt % 1,2-propanediol, and 10 wt % 1,2-butanediol) was added in a dehydration reactor. After the mixture was heated to 180° C., 2 g of 300-mesh HZSM-5 zeolite with a $SiO_2/Al_2O_3$ ratio of 25 was added. With stirring, the volatile products generated from the dehydration of miscellaneous polyols were continuously evaporated for 4 h.

(b) Separation of the catalyst: After the dehydration reaction, the zeolite was separated from the liquid product with a centrifuge at a speed of 6000 rpm.

(c) Further purification via distillation: after the previous step, the liquid mixture in the reactor was separated via vacuum distillation at an overhead pressure of 10 kPa and bottom temperature of 135-150° C. ~65 g of ethylene glycol product at a purity of >90 wt % was obtained via simple distillation, in which the content of 1,2-butanediol was <1 wt %. The residue at the bottom was used to produce antifreezes.

(d) Removal of miscellaneous polyols via distillation: after the reaction, a small amount of 1,2-propanediol and 1,2-butanediol was still not reacted. These impurities were removed via vacuum distillation at a bottom temperature of 115-130° C. and an overhead pressure of 10 kPa. After the distillation, the purified ethylene glycol product was at a purity of >98 wt %.

(e) Gas-liquid separation: the evaporated volatile products in step 1 contained acetals, ketals (trace amount), moisture, acetone, propanal, and other low-boiling-point substances. In addition, a small amount of vapor of polyols was also mixed into the volatile products. 20 g of volatile products were liquefied and obtained with a condenser at 10° C.

(f) Liquid-liquid separation: the liquefied volatile products in the previous step were transferred into a decanter to be separated into 12 g of oil-phase product and 8 g of aqueous product.

(g) Concentration of aldehydes and ketones in the aqueous product: the aqueous product obtained in the previous step was separated via atmospheric distillation. The overhead (condenser) temperature was 8° C. and the bottom (reboiler) temperature was ~92° C. The distillate was a mixture of acetaldehyde, propanal, and acetone, and an aqueous solution of dioxane was also recovered in the bottom, which was then concentrated through steam stripping for further utilization.

(h) Preliminary separation of the oil-phase product: the oil-phase product obtained instep 5 was preliminarily separated via atmospheric distillation into five products: aldehydes/ketones (boiling point: 20-60° C.), low-boiling-point acetals (boiling point: 70-90° C.), raw dioxane (boiling point: 90-100° C.), high-boiling-point acetals (boiling point: 110-140° C.), and high-boiling-point oxygenates (boiling point: 140-190° C.). Among them, the mixture of aldehydes/ketones was mixed with those obtained in the step 7 for further separation via distillation.

(i) Separation of acetals and ketals: the raw acetals in the previous step, containing a small amount of ketals, were the most abundant substances in the crude oil-phase product (~4 g). Wherein, low-boiling-point acetals (mainly 2-ethyl-1,3-dioxolane and 2-ethyl-4-methyl-1,3-dioxolane) accounted for ~60 wt %. High-boiling-point acetals (mainly 2-propyl-1,3-dioxolane and 2-isopropyl-4-methyl-1,3-dioxolane) accounted for ~40 wt %. The low- and high-boiling-point acetals were then separated with two distillation columns independently. Finally, four pure acetal products were obtained.

(j) Regeneration of the catalyst: the spent HZSM-5 zeolite was regenerated through calcination at 550-580° C.

EXAMPLE 2

(a) Dehydration reaction: 100 mL of crude ethylene glycol (73 wt % ethylene glycol, 17 wt % 1,2-propanediol, and 10 wt % 1,2-butanediol) was added in a dehydration reactor. After the mixture was heated to 185° C., 5 g of 300-mesh Hβ zeolite with a$SiO_2/Al_2O_3$ratio of 25 was added. With stirring, the volatile products generated from the dehydration of miscellaneous polyols were continuously evaporated for 4 h.

(b) Separation of the catalyst: After the dehydration reaction, the zeolite was separated from the liquid product with a vacuum filter.

(c) Purification via distillation: after the previous step, the liquid mixture in the reactor was separated via vacuum distillation at an overhead pressure of 10 kPa. ~65 g of raw ethylene glycol product (b.p. <150° C.) at a purity of >97.5 wt % was obtained via the vacuum distillation. The content of 1,2-butanediol was <0.5 wt % and the content of 1,2-propanediol was <2 wt % in the product. The residue at the bottom was used to produce antifreezes.

(d) Removal of miscellaneous polyols via distillation: the unreacted 1,2-propanediol was removed via vacuum distillation at a bottom temperature of 115-130° C. and an overhead pressure of 10 kPa. After the distillation, the purified ethylene glycol product was at a purity of 99.5 wt %.

(e) Gas-liquid separation: the evaporated volatile products in step 1 contained acetals, ketals (trace amount), moisture, acetone, propanal, and other low-boiling-point substances. In addition, a small amount of vapor of polyols was also mixed into the volatile products. ~34 g of volatile products were liquefied and obtained with a condenser at 10° C.

(f) Liquid-liquid separation: the liquefied volatile products in the previous step were transferred into a decanter to be separated into 24.9 g of oil-phase product and 9.1 g of aqueous product.

(g) Concentration of aldehydes and ketones in the aqueous product: the aqueous product obtained in the previous step was separated via atmospheric distillation. The overhead (condenser) temperature was 8° C. and the bottom (reboiler) temperature was ~92° C. The distillate was a mixture of acetaldehyde, propanal, and acetone, and an aqueous solution of dioxane was also recovered in the bottom, which was then concentrated through air stripping for further utilization.

(h) Preliminary separation of the oil-phase product: the oil-phase product obtained in step 5 was preliminarily separated via atmospheric distillation into five products: aldehydes/ketones (boiling point: 20-60° C.), low-boiling-point acetals (boiling point: 70-90° C.), raw dioxane (boiling point: 90-100° C.), high-boiling-point acetals (boiling point: 110-140° C.), and high-boiling-point oxygenates (boiling point: 140-190° C.). Among them, the mixture of aldehydes/ketones was mixed with those obtained in the step 7 for further separation via distillation.

(i) Separation of acetals and ketals: the raw acetals in the previous step, containing a small amount of ketals, were the most abundant substances in the crude oil-phase product (~20 g). Wherein, low-boiling-point acetals (mainly 2-ethyl-1,3-dioxolane and 2-ethyl-4-methyl-1,3-dioxolane) accounted for ~60 wt %. High-boiling-point acetals (mainly 2-propyl-1,3-dioxolane and 2-isopropyl-4-methyl-1,3-dioxolane) accounted for ~40 wt %. The low- and high-boiling-point acetals were then separated with two distillation columns independently. Finally, four pure acetal products were obtained.

(j) Regeneration of the catalyst: the spent HP zeolite was regenerated through calcination at 650-700° C.

EXAMPLE 3

(a) Batch reactive distillation: 100 g of HZSM-5 zeolite with a $SiO_2/Al_2O_3$ ratio of 25 was loaded in the lower reaction zone of a batch reactive distillation column. 100 g of packing was loaded in the upper distillation zone. 100 mL of crude ethylene glycol (73 wt % ethylene glycol, 17 wt % 1,2-propanediol, and 10 wt % 1,4-butanediol) was added in the bottom of the distillation column. The mixture in the bottom was heated to 180-190° C. and the overhead temperature was 10° C. 22 g of distillate was obtained after 3 h.

(b) Further purification via distillation: after the previous step, the liquid mixture in the bottom was further separated via another vacuum distillation column at an overhead pressure of 10 kPa and bottom temperature of 135-150° C. ~67 g of raw ethylene glycol product at a purity of >93 wt % was distilled. The residue at the bottom was used to produce antifreezes.

(c) Removal of miscellaneous polyols via distillation: the unreacted 1,2-propanediol was further removed via vacuum distillation at a bottom temperature of 115-130° C. and an overhead pressure of 10 kPa. After the distillation, the purified ethylene glycol product was at a purity of >99.3 wt %.

(d) Liquid-liquid separation: the distillate in step 1 was transferred into a decanter to be separated into 13 g of oil-phase product and 9 g of aqueous product.

(e) Concentration of aldehydes and ketones in the aqueous product: the aqueous product obtained in the previous step was separated via atmospheric distillation. The overhead (condenser) temperature was 8° C. and the bottom (reboiler) temperature was ~92° C. The distillate was a mixture of acetaldehyde, propanal, and acetone, and an aqueous solution of dioxane was also recovered in the bottom, which was then concentrated through steam stripping for further utilization.

(f) Preliminary separation of the oil-phase product: the oil-phase product obtained was preliminarily separated via atmospheric distillation into five products: aldehydes/ketones (boiling point: 20-60° C.), low-boiling-point acetals (boiling point: 70-90° C.), raw dioxane (boiling point: 90-100° C.), high-boiling-point acetals (boiling point: 110-140° C.), and high-boiling-point oxygenates (boiling point: 140-190° C.). Among them, the mixture of aldehydes/ketones was further separated via distillation.

(g) Separation of acetals and ketals: the raw acetals in the previous step, containing a small amount of ketals, were the most abundant substances in the crude oil-phase product (~4 g). Wherein, low-boiling-point acetals accounted for ~60 wt % and high-boiling-point acetals accounted for ~40 wt %. The low- and high-boiling-point acetals were then separated with two distillation columns independently. Finally, four pure acetal products were obtained.

(h) Catalyst regeneration: Regeneration of the catalyst: the spent HZSM-5 zeolite was regenerated through calcination at 650-750° C.

EXAMPLE 4

(a) Dehydration reaction: 100 mL of crude ethylene glycol (85 wt % ethylene glycol, 10 wt % 1,2-propanediol, and 5 wt % 1,3-butanediol) was added in a dehydration reactor. After the mixture was heated to 185° C., 4 g of 98 wt % sulfuric acid was added. With stirring, the volatile products generated from the dehydration of miscellaneous polyols were continuously evaporated for 4 h.

(b) Separation of sulfuric acid and purification via distillation: After the dehydration reaction, the liquid in the reactor was separated via vacuum distillation at an overhead pressure of 10 kPa and bottom temperature of 135-150° C. 67 g of raw ethylene glycol at a purity of >96 wt % was distilled.

(c) Removal of miscellaneous polyols via distillation: the unreacted 1,2-propanediol was further removed via vacuum distillation at a bottom temperature of 115-130° C. and an overhead pressure of 10 kPa. After the distillation, the purified ethylene glycol product was at a purity of >99.2 wt %.

(d) Gas-liquid separation: the evaporated volatile products in step 1 contained acetals, ketals (trace amount), moisture, acetone, propanal, and other low-boiling-point substances. In addition, a small amount of vapor of polyols was also mixed into the volatile products. 13 g of volatile products were liquefied and obtained with a condenser at 10° C.

(e) Liquid-liquid separation: the liquefied volatile products in the previous step were transferred into a decanter to be separated into 9 g of oil-phase product and 4 g of aqueous product.

(f) Concentration of aldehydes and ketones in the aqueous product: the aqueous product obtained in the previous step was separated via atmospheric distillation. The overhead (condenser) temperature was 8° C. and the bottom (reboiler) temperature was ~92° C. The distillate was a mixture of acetaldehyde, propanal, and acetone, and an aqueous solution of dioxane was also recovered in the bottom, which was then concentrated through air stripping for further utilization.

(g) Preliminary separation of the oil-phase product: the oil-phase product obtained in step 5 was preliminarily separated via atmospheric distillation into five products: aldehydes/ketones (boiling point: 20-60° C.), low-boiling-point acetals (boiling point: 70-90° C.), raw dioxane (boiling point: 90-100° C.), high-boiling-point acetals (boiling point: 110-140° C.), and high-boiling-point oxygenates (boiling point: 140-190° C.). Among them, the mixture of aldehydes/ketones was mixed with those obtained in step 6 for further separation via distillation.

(h) Separation of acetals and ketals: the raw acetals in the previous step, containing a small amount of ketals, were the most abundant substances in the crude oil-phase product (~4 g). Wherein, low-boiling-point acetals accounted for ~60 wt % and high-boiling-point acetals accounted for ~40 wt %. The low- and high-boiling-point acetals were then separated with two distillation columns independently. Finally, four pure acetal products were obtained.

(i) Regeneration of the catalyst: the residue in the bottom in step 2 contained sulfuric acid and diethylene glycol. The sulfuric acid was separated and regenerated through vacuum distillation.

EXAMPLE 5

(a) Dehydration reaction: 100 mL of crude ethylene glycol (60 wt % ethylene glycol, 25 wt % 1,2-propanediol, and 15 wt % 2,3-butanediol) was added in a dehydration reactor. After the mixture was heated to 185° C., 3 g of 300-mesh HZSM-5 zeolite with a$SiO_2/Al_2O_3$ratio of 25 was added. With stirring, the volatile products generated from the dehydration of miscellaneous polyols were continuously evaporated for 4 h.

(b) Separation of the catalyst: After the dehydration reaction, the zeolite was separated from the liquid product with a centrifuge.

(c) Further purification via distillation: after the previous step, the liquid mixture in the reactor was separated via vacuum distillation at an overhead pressure of 10 kPa and bottom temperature of 135-150° C. ~53 g of ethylene glycol product at a purity of >84 wt % was obtained via simple distillation, in which the content of 2,3-butanediol was <1 wt %. The residue at the bottom was used to produce antifreezes.

(d) Removal of miscellaneous polyols via distillation: the unreacted 1,2-propanediol was further removed via vacuum distillation at a bottom temperature of 115-130° C. and an overhead pressure of 10 kPa. After the distillation, the purified ethylene glycol product was at a purity of >99 wt %.

(e) Gas-liquid separation: the evaporated volatile products in step 1 contained acetals, ketals (trace amount), moisture, acetone, propanal, and other low-boiling-point substances. In addition, a small amount of vapor of polyols was also mixed into the volatile products. 34 g of volatile products were liquefied and obtained with a condenser at 10° C.

(f) Liquid-liquid separation: the liquefied volatile products in the previous step were transferred into a decanter to be separated into 20 g of oil-phase product and 14 g of aqueous product.

(g) Concentration of aldehydes and ketones in the aqueous product: the aqueous product obtained in the previous step was separated via atmospheric distillation. The overhead (condenser) temperature was 8° C. and the bottom (reboiler) temperature was ~92° C. The distillate was a mixture of acetaldehyde, propanal, and acetone, and an aqueous solution of dioxane was also recovered in the bottom, which was then concentrated through steam stripping for further utilization.

(h) Preliminary separation of the oil-phase product: the oil-phase product obtained in step 5 was preliminarily separated via atmospheric distillation into five products: aldehydes/ketones (boiling point: 20-60° C.), low-boiling-point acetals (boiling point: 70-90° C.), raw dioxane (boiling point: 90-100° C.), high-boiling-point acetals (boiling point: 110-140° C.), and high-boiling-point oxygenates (boiling point: 140-190° C.). Among them, the mixture of aldehydes/ketones was mixed with those obtained in the step 7 for further separation via distillation.

(i) Separation of acetals and ketals: the raw acetals in the previous step, containing a small amount of ketals, were the most abundant substances in the crude oil-phase product (~8.5 g). Wherein, low-boiling-point acetals accounted for ~60 wt %. The low- and high-boiling-point acetals were then separated with two distillation columns independently. Finally, four pure acetal products were obtained.

(j) Regeneration of the catalyst: the spent HZ SM-5 zeolite was regenerated through calcination at 700-750° C.

EXAMPLE 6

(a) Reactive Distillation: 1.2 t of Hβ zeolite with a$SiO_2/Al_2O_3$ratio of 160 was loaded in the lower reaction zone of a reactive distillation column. 1 t of packing was loaded in the upper distillation zone. Crude ethylene glycol (73 wt % ethylene glycol, 17 wt % 1,2-propanediol, and 10 wt % 1,2-butanediol) was pumped into the middle of the distillation column at a flow rate of 1 t/h. The mixture in the bottom was heated to 185° C. and the overhead temperature was 10° C. The distillate was obtained at a rate of 200 kg/h.

(b) Further purification via distillation: after the previous step, the liquid mixture in the bottom was further separated via another vacuum distillation column at an overhead pressure of 10 kPa and bottom temperature of 140° C. Raw ethylene glycol product at a purity of >96 wt % was distilled at a rate of 630 kg/h, in which the content of 1,2-butanediol was <0.4 wt %. The residue at the bottom was used to produce antifreezes.

(c) Removal of miscellaneous polyols via distillation: the unreacted 1,2-propanediol was further removed via vacuum distillation at a bottom temperature of 115-130° C. and an overhead pressure of 10 kPa. After the distillation, the purified ethylene glycol product was at a purity of >99.7 wt % and a flow rate of 610 kg/h.

(d) Liquid-liquid separation: the distillate in step 1 was transferred into a decanter to be separated into oil-phase product at a rate of 230 kg/h and aqueous product at a rate of 110 kg/h.

(e) Concentration of aldehydes and ketones in the aqueous product: the aqueous product obtained in the previous step was separated via atmospheric distillation. The overhead (condenser) temperature was 8° C. and the bottom (reboiler) temperature was ~92° C. The distillate was a mixture of acetaldehyde, propanal, and acetone, and an aqueous solution of dioxane was also recovered in the bottom, which was then concentrated through air stripping for further utilization.

(f) Preliminary separation of the oil-phase product: the oil-phase product obtained was preliminarily separated via atmospheric distillation into five products: aldehydes/ketones (boiling point: 20-60° C.), low-boiling-point acetals (boiling point: 70-90° C.), raw dioxane (boiling point: 90-100° C.), high-boiling-point acetals (boiling point: 110-140° C.), and high-boiling-point oxygenates (boiling point: 140-190° C.). Among them, these aldehydes/ketones were mixed with those aldehydes/ketones obtained in step 5, and the mixture was further separated via distillation.

(g) Separation of acetals and ketals: the raw acetals in the previous step, containing a small amount of ketals, were the most abundant substances in the crude oil-phase product. The flow rate of the raw acetals was 197 kg/h, in which low-boiling-point acetals (mainly 2-ethyl-1,3-dioxolane and 2-ethyl-4-methyl-1,3-dioxolane) accounted for ~60 wt % and high-boiling-point acetals (mainly 2-propyl-1,3-dioxolane and 2-isopropyl-4-methyl-1,3-dioxolane) accounted for ~40 wt %. The low- and high-boiling-point acetals were then separated with two distillation columns independently. Finally, four pure acetal products were obtained.

(h) Regeneration of the catalyst: the spent Hβ zeolite was regenerated at 550-600° C. through calcination in an industrial furnace.

These examples illustrate the invention but should not be interpreted as a limitation thereon.

We claim:

1. A method for separating a close-boiling mixture of ethylene glycol and one or more miscellaneous polyols selected from the group consisting of 1,2-propanediol, 1,3-propanediol, 1,2-butanediol, 1,2-pentanediol, 1,2-hexanediol, 1,3-butanediol, 2,3-butanediol, 1,4-butanediol, andglycerol, the method comprising:
   (a) mixing the close-boiling mixture with an acid catalyst at a temperature higher than 150° C.;
   (b) performing a dehydration reaction in a reactor under at an elevated temperature;
   (c) converting the miscellaneous polyols into volatile products via dehydration, acetalization, and ketalization reactions; and
   (d) removing the volatile products via vaporization or distillation, thereby removing the miscellaneous polyols from the closed-boiling mixture to obtain ethylene glycol as a product.

2. The method of claim 1, wherein said acid catalyst is selected from the group consisting of liquid Brønsted acids, solid Brønsted acids, Lewis acids, acid-site-containing oxides, acid-site-containing minerals, and combinations thereof.

3. The method of claim 1, wherein the ethylene glycol product is further purified to remove the residual miscellaneous polyols via distillation, extraction, crystallization, adsorption, chromatography, or combinations thereof.

4. The method of claim 1, wherein the unconverted material in the dehydration reactor contains ethylene glycol and acid catalysts;
   (a) when only solid acid catalysts are used, the catalysts are removed from ethylene glycol through solid-liquid separation, evaporation or distillation; the removed solid acid is regenerated via calcination or elution or drying for the recycling of solid catalysts;
   (b) when only liquid acid catalysts are used, the catalysts are removed from ethylene glycol through evaporation or distillation for the recycling of liquid catalysts; the liquid acid catalysts are neutralized with an alkali and then the product of the neutralization reaction is removed from ethylene glycol through evaporation or crystallization; and
   (c) when both solid and liquid acid catalysts are used, the solid catalysts are firstly removed from ethylene glycol through solid-liquid separation; the liquid acid catalysts are removed from ethylene glycol through evaporation or distillation; or, ethylene glycol is directly separated from both solid and liquid acid catalysts via evaporation or distillation.

5. The method of claim 1, wherein volatile products of miscellaneous polyols in the dehydration, acetalization, and ketalization reactions are vaporized, condensed, and collected; (b) the removed products include volatile oil-phase and aqueous products; (c) the oil-phase and aqueous products are then separated; (d) the oil-phase product is further separated into acetals, ketals, dioxanes, aldehydes, and ketones; apart from the removal of miscellaneous polyols, by-products of acetals, ketals, cyclic ethers, acyclic ethers, aldehydes, and ketones are co-produced; (e) the dehydration reactor itself also functions as a simple reactive distillation apparatus to remove the by-products from ethylene glycol; or, these by-products are produced and removed via multistage reactive distillation; or, the reaction system are refluxed in the reactor, and then the mixture is separated through decantation, extraction, adsorption, or distillation.

6. The method of claim 1, wherein the feedstock contains 50 wt %-95 wt % ethylene glycol and 5 wt %-50 wt % of the miscellaneous polyols.

7. The method of claim 1, wherein said acid catalyst is selected from the group consisting of H-form molecular sieves, sulfonated activated carbon, H-form resins, sulfuric acid, hydrochloric acid, and nitric acid; and said acid catalyst accounts for 0.1 wt %-15 wt % of a total weight of the dehydration reaction mixture.

8. The method of claim 1, wherein the dehydration reaction takes place at 150-198° C. and a reaction pressure is atmospheric pressure.

9. The process of claim 1, wherein the close-boiling mixture is synthesized from coal or biomass.

10. The method of claim 1, wherein the solid-liquid separation is carried out in a pressure filter, a vacuum filter, a settler, or a centrifuge.

11. The method of claim 2, wherein said acid catalyst is selected from the group consisting of H-form molecular sieves, sulfonated activated carbon, H-form resins, sulfuric acid, hydrochloric acid, and nitric acid; and said acid catalyst accounts for 0.1 wt %-15 wt % of a total weight of the dehydration reaction mixture.

* * * * *

UNITED STATES PATENT AND TRADEMARK OFFICE
CERTIFICATE OF CORRECTION

Page 1 of 1

PATENT NO. : 9,926,251 B2
APPLICATION NO. : 15/521033
DATED : March 27, 2018
INVENTOR(S) : Tao Zhang et al.

It is certified that error appears in the above-identified patent and that said Letters Patent is hereby corrected as shown below:

On the Title Page

Item (72) should read:
Inventors: Tao Zhang, Liaoning (CN); Shuo Ai, Liaoning (CN); Mingyuan Zheng, Liaoning (CN); Aiqin Wang, Liaoning (CN); Weizhen Li, Liaoning (CN); Xiaodong Wang, Liaoning (CN)

Signed and Sealed this
Tenth Day of September, 2019

Andrei Iancu
*Director of the United States Patent and Trademark Office*